United States Patent [19]

Bouillon et al.

[11] 4,073,898
[45] Feb. 14, 1978

[54] COMPOSITION FOR REDUCING THE OILY APPEARANCE OF THE HAIR AND SKIN

[75] Inventors: Claude Bouillon, Eaubonne; Claudine Berrebi, Paris, both of France

[73] Assignee: L'Oreal, Paris, France

[21] Appl. No.: 645,658

[22] Filed: Dec. 31, 1975

[30] Foreign Application Priority Data

Dec. 31, 1974 France .................. 74 43406

[51] Int. Cl.² ................ A61K 31/615; A61K 31/205; C07C 147/14
[52] U.S. Cl. .................. 424/233; 260/295.5 S; 260/326.82; 260/501.12; 260/501.19; 260/501.21; 260/553 A; 260/570.5 S; 260/583 EE; 424/DIG. 1; 424/DIG. 2; 424/DIG. 4; 424/266; 424/274; 424/316; 424/322; 424/325; 424/330
[58] Field of Search ................. 424/325, 330, DIG. 4, 424/316, 233; 260/501.21, 501.12, 501.19

[56] References Cited

U.S. PATENT DOCUMENTS

| | | | |
|---|---|---|---|
| 2,835,704 | 5/1958 | Walton | 260/562 |
| 3,109,777 | 11/1963 | Zviak | 424/74 |
| 3,803,323 | 4/1974 | Kalopissis | 424/322 |
| 3,968,218 | 7/1976 | Bouillon et al. | 424/316 X |

FOREIGN PATENT DOCUMENTS 1,085,513   7/1954   France .................. 260/501.21

*Primary Examiner*—Albert T. Meyers
*Assistant Examiner*—Vera C. Clarke
*Attorney, Agent, or Firm*—Cushman, Darby & Cushman

[57] ABSTRACT

A composition for treating oily hair or skin to reduce the oily appearance thereof comprises in an appropriate vehicle an active compound having the formula

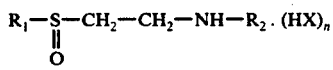

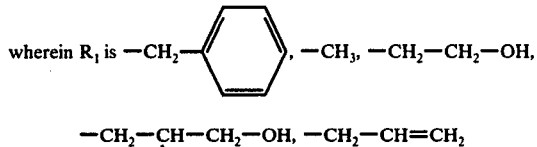

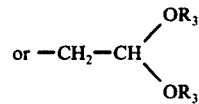

wherein $R_3$ is lower alkyl containing 1–3 carbon atoms; $n = 0$ or 1 with the proviso that when $n = 0$,

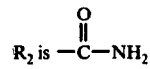

and when $n = 1$, $R_2$ is hydrogen; and HX represents a mineral or organic acid. The composition can be applied topically or be orally administered to a person whose hair or skin has an oily appearance to reduce said oily appearance.

17 Claims, No Drawings

COMPOSITION FOR REDUCING THE OILY APPEARANCE OF THE HAIR AND SKIN

The present invention relates to a composition for combatting a greasy and unaesthetic appearance of the hair and to a composition for improving the appearance of the skin. These compositions can be used topically or orally.

Numerous compounds have already been proposed for the treatment of oily hair as well as unaesthetic appearing skin. Among these compounds certain cysteamine derivatives have been proposed. For instance, there has been proposed cysteamine derivatives having the formula $$R - S - CH_2 - CH_2 - NH - R' \quad (I)$$

wherein

R represents $-CH_2-C_6H_5$, $-CH_2-COOH$, $-C(C_6H_5)_3$ or a saturated or unsaturated, linear or branched hydrocarbon radical having up to 20 carbon atoms, capable of carrying one or several alcohol functions of which one can be terminal, and R' represents either hydrogen or a $-COR''$ or $-SO_2R''$ radical in which $R''$ represents lower alkyl or aryl.

Although these compounds are disclosed as being excellent agents for the treatment of oily or greasy hair and the unaesthetic appearance of the skin, their use has been found to be somewhat limited due to the odor of sulfur which is emitted from the hair or skin after application of these compositions and due to the fact that certain of the compounds corresponding to formula I above cause slight irritation of the scalp or skin.

However, it has now surprisingly been found that the oxidation of certain ones only of these cysteamine derivatives completely suppresses these drawbacks while at the same time preserving the excellent ability of these compounds to reduce the oily or greasy appearance of the hair and the skin.

In effect, the thioether derivatives of the cysteamine of formula I above can, by controlled oxidation, lead either to the formation of sulfoxides or to the formation of sulfones. It has now surprisingly been found that only the sulfoxide type compounds provide the desired results.

The sulfone type oxidation derivatives on the other hand exhibit an activity clearly inferior to that of their corresponding thioethers or sulfoxides.

The present invention thus relates to a composition for the treatment of oily hair and skin, this composition containing in an appropriate vehicle or carrier at least one active compound having the formula $$R_1 - \overset{\overset{O}{\|}}{\underset{}{S}} - CH_2 - CH_2 - NH - R_2 \cdot (HX)_n \quad (II)$$

wherein $R_1$ represents a member selected from the group consisting of

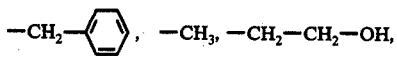, $-CH_3$, $-CH_2-CH_2-OH$,

-continued

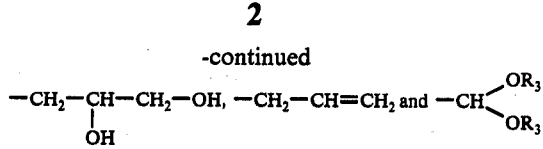

wherein $R_3$ represents lower alkyl having 1-3 carbon atoms, $n = 0$ or 1 and when $n = 0$, $R_2$ represents

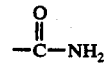

and when $n = 1$, $R_2$ represents hydrogen and

HX represents a mineral or organic acid.

Representative mineral and organic acids include, without limitation, hydrochloric acid, hydrobromic acid, sulfuric acid, tartaric acid, nicotinic acid, malic acid, glutamic acid, salicylic acid, fumaric acid, 5-amino-3-thia hexanedioic acid and 5-pyrrolidone-2-carboxylic acid.

Representative active compounds which can be used in the composition of the present invention include:
2-benzylsulfinyl ethylammonium hydrochloride,
2-methylsulfinyl ethylammonium hydrochloride,
2-methylsulfinyl ethylammonium malate,
2-benzylsulfinyl ethylammonium tartrate,
2-β-hydroxy ethylsulfinyl ethylurea,
2-methylsulfinyl ethylurea,
2-(2,3-dihydroxy propylsulfinyl) ethylurea,
2-benzylsulfinyl ethylurea,
2-benzylsulfinyl ethylammonium 5-amino-3-thia hexanedioate,
2-methylsulfinyl ethylammonium 5-amino-3-thia hexanedioate,
2-(2,2'-dimethoxy ethylsulfinyl) ethylammonium malate,
2-(2,2'-diethoxy ethylsulfinyl) ethylammonium malate,
2-(2,3-dihydroxy propylsulfinyl) ethylammonium hydrochloride,
2-methylsulfinyl ethylammonium nicotinate,
2-methylsulfinyl ethylammonium salicylate,
2-benzylsulfinyl ethylammonium nicotinate,
2-benzylsulfinyl ethylammonium salicylate,
2-allyl sulfinyl ethylurea,
2-methylsulfinyl ethylammonium 5-pyrrolidone-2-carboxylate,
2-benzylsulfinyl ethylammonium 5-pyrrolidone-2-carboxylate,
2-(2,2'-diethoxy ethylsulfinyl) ethylurea and
2-(2,2'-dimethoxy ethylsulfinyl) ethylurea.

The present invention relates particularly to a cosmetic composition for combatting against an oily and unaesthetic appearance of the hair. The composition contains at least one active compound of formula II above, in suspension or in solution in water, in an alcohol such as ethanol or isopropanol, in a hydroalcoholic solution, in an oil, in an emulsion, in a cream, or in a gel.

The concentration of the active compound is, generally, between 0.1 and 10 and preferably between 1 and 3 percent by weight based on the total weight of the composition.

These compositions can contain the active compounds, as defined above, either alone, or in admixture, or even in admixture with other compounds already known for use in combatting against an oily and unaesthetic appearance of the hair.

Further, these compositions can also contain such adjuvants as penetrating agents or perfumes which are generally employed in cosmetic compositions.

The present invention also relates to a process for treating oily hair in order to improve its appearance said process comprising applying to the scalp, with rubbing, the composition as defined above.

The cosmetic compositions according to the invention can also comprise a dry shampoo in powder or aerosol form without a surface-active agent. Such a composition can be applied to dry hair. When so used, the composition is left in contact with the hair for a period of time after which it is removed by simply brushing the hair.

The composition of the present invention can also be provided as a hair lacquer or hair setting lotion containing at least one active compound in combination, in an appropriate cosmetic vehicle or carrier, with at least one conventional cosmetic resin.

Representative cosmetic resins include polyvinylpyrrolidone, copolymers of vinyl pyrrolidone and vinyl acetate, copolymers of vinyl acetate and an unsaturated carboxylic acid such as crotonic acid, copolymers resulting from the polymerization of vinyl acetate, crotonic acid and an acrylic or methacrylic ester, copolymers resulting from the copolymerization of vinyl acetate and an alkyl vinyl ether, copolymers resulting from the copolymerization of vinyl acetate, crotonic acid and a vinyl ester of a long carbon chain acid or even of an allyl or methallyl ester of a long carbon chain acid, copolymers resulting from the copolymerization of an ester of an unsaturated alcohol and a short carbon chain carboxylic acid, of a short carbon chain unsaturated acid and at least one long carbon chain ester and copolymers resulting from the polymerization of at least one unsaturated ester and at least one unsaturated acid.

In a particular embodiment, the cosmetic resins included in the compositions according to the invention can have lateral chains on which are found thiol functions.

The cosmetic resins contained in these hair lacquer or hair setting lotion compositions can also be colored polymers, i.e. polymers containing in their macromolecular chain one or more dye molecules which impart to the hair a particular color or shade.

These hair lacquer or hair setting lotion compositions can also contain a direct dye so as to impart a color or shade to the hair or even such conventional adjuvants as penetrating agents, cationic compounds, quaternary ammonium salts, vitamins, proteins, peptides which can be more or less hydrolyzed, derivatives of starch or cellulose, surface-active agents, dyes, perfumes and the like.

The cosmetic vehicle usefully employed in the production of hair lacquer or hair setting lotion compositions can be those conventionally employed in these types of compositions.

Generally the cosmetic vehicle or carrier is an alcohol or a hydroalcoholic solution so as to provide a hair setting lotion, or the carrier can be an alcohol hydroalcoholic solution admixed with an appropriate amount of a liquified gaseous propellant under pressure and packaged in an aerosol container so as to provide a hair lacquer composition.

In these hair lacquer or hair setting lotion compositions the amount of the active compound present is generally between 0.1 and 10, but preferably between 1-3 weight percent, while the amount of the cosmetic resin ranges between preferably 0.1 and 10 percent by weight, based on the total weight of the composition.

With these hair lacquer or hair setting lotion compositions, the hair can be treated not only to combat against a greasy or oily appearance but also to style the hair. This overall operation comprises applying the said composition to the roots of the hair and to the scalp, permitting the hair to dry, or alternatively, rolling the hair on rollers before letting it dry.

The cosmetic compositions according to the invention can also be provided as a treating shampoo for combatting against an oily and unaesthetic appearance of the hair, said shampoo having a clear, opaque or pearly liquid appearance or even the appearance of a cream or gel.

These shampoo compositions comprise, in combination, at least one anionic, cationic, nonionic or amphoteric detergent and at least one active compound of formula II as defined above.

Representative anionic detergents include alkyl sulfates, alkyl ether sulfates, alkyl polyether sulfates, alkyl sulfonates wherein the alkyl moiety contains from 8-18 carbon atoms, sulfated monoglycerides, sulfone monoglycerides, sulfated alkanolamides, sulfone alkanolamides, soaps of fatty acids, monosulfosuccinates of fatty alcohols, the condensation product of fatty acids with isethionic acid, the condensation product of fatty acids with methyl taurine, the condensation product of fatty acids with sarcosine and the condensation product of fatty acids with protein hydrolyzate.

Representative cationic detergents include long chain quaternary ammoniums, esters of fatty acids and amino alcohols and polyether amines.

Representative non-ionic detergents include esters of polyols and sugars, the condensation product of ethylene oxide on fatty acids, on fatty alcohols, on long chain alkylphenols, on long chain mercaptans and on long chain amides and the polyethers of polyhydroxylated fatty alcohols.

Representative amphoteric detergents include asparagine derivatives, the condensation product of monochloroacetic acid on imidazolines, the alkyl amino propionates, betainic derivatives and amine oxides.

These shampoo compositions generally contain from 0.1 to 10, but preferably from 1 to 3 percent by weight of the active compound as defined above based on the total weight of the composition. They also contain for example from 4 to 20 and preferably from 5 to 10 percent by weight of a detergent in solution in an aqueous medium.

The shampoos as defined above can also contain conventional cosmetic adjuvants such as perfumes and dyes. They can also contain thickeners such as alkanolamides of fatty acids, cationic polymers such as the copolymers of quaternized vinyl pyrrolidone, cationic cellulosic polymers and the like, cellulose derivatives such as carboxymethyl cellulose or hydroxy methyl cellulose, esters of long chain polyols and natural gums, in a manner to provide them in the form of a cream or gel.

Finally, these shampoo compositions can be provided as a powder which can either be applied to moist hair or be dissolved in a given volume of water before washing the hair.

These shampoo compositions can also include one or more dyes and be employed to color the hair.

With these shampoo compositions the hair can be treated to combat against an oily appearance thereof by applying an effective amount of the same to the hair which optionally can previously be wetted, massaging the scalp for a period of a few minutes and then rinsing the hair.

Generally satisfactory results are obtained by weekly use of the shampoo, which regimen significantly reduces and, in certain cases, completely suppresses the oily appearance of the hair, while at the same time assures normal care of the hair.

It has also been found that the active compounds as defined above can together with an appropriate cosmetic vehicle be topically applied to the skin to improve its appearance. These compositions are present, preferably, in the form of creams, milks, gels, dermatologic cakes or aerosol foams. They can also be present in the form of aqueous or hydroalcoholic solutions. Generally these compositions for topical application to the skin contain from 0.1 to 5 weight percent of the active compound as defined above. These compositions can also contain conventional adjuvants such as fatty bodies, emulsifying agents, preservatives, perfumes, dyes, and waxes. They can also contain colored pigments which dye the skin and mask skin defects.

With these compositions, the skin can be treated to improve its appearance by applying the same to desired portions of the skin.

The active compounds as defined above can also be employed in orally administered compositions for combatting against an oily and unaesthetic appearance of the hair. Such a treatment provides numerous advantages and, in particular, it permits the treatment of oily hair without having to apply products to the scalp thereby avoiding any disturbance of coiffured hair.

These orally administered compositions generally contain the active compound in an amount between 0.01 and 50 percent by weight, based on the total weight of the composition, but preferably between 5 and 25%. The active compound can be provided in solution in an alimentary liquid such as an aqueous or hydroalcoholic solution, which can be optionally flavored.

The active compound can also be incorporated in a solid ingestible excipient and be present for example in the form of granules, pills, tablets or lozenges. They can also be provided in solution in an alimentary liquid packaged in an ingestible capsule.

It has been found that the active compounds in accordance with the invention are non-toxic.

The use of these orally administered compositions can be left to the free discretion of the user. However, it is considered advisable to use these compositions for successive periods of 15 days, with an interruption of 15 days, at a dosage level in the order of 100 mg per 24 hours.

With these compositions an oily and unaesthetic appearance of the hair can be reduced or eliminated by orally administering the same to a person having hair which is oily or greasy in appearance.

EXAMPLES OF COMPOSITIONS

EXAMPLE 1

In accordance with the present invention, a lotion, for daily use, in the treatment of oily hair is prepared by admixing:

| | |
|---|---|
| 2-methylsulfinyl ethylurea | 0.2 g |
| Ethyl alcohol, 50°, q.s.p. | 100 ml |
| Perfume | 0.1 g |
| Dye | 0.1 g |

The use of this composition provides a very clear reduction of the oily appearance of the hair.

Example 1 is repeated except that active compound is advantageously replaced by the same amount of 2-allylsulfinyl ethylurea.

EXAMPLE 2

An orally administered composition in the form of drops is prepared by admixing:

| | |
|---|---|
| 2-benzylsulfinyl ethylammonium hydrochloride | 1 g |
| Glycerine | 40 g |
| Ethyl alcohol | 30 g |
| Water, q.s.p. | 100 g |
| Lemon tincture, sufficient to flavor the composition | |

This composition, taken orally, during a 15 day treatment period provides a clear improvement in the appearance of the hair and scalp.

EXAMPLE 3

A capillary lotion for oily hair is prepared by admixing:

| | |
|---|---|
| Calcium pantothenate | 0.5 g |
| 2-methylsulfinyl ethylammonium malate | 0.3 g |
| Perfume | 0.1 g |
| Ethyl alcohol, 40°, q.s.p. | 100 ml |

Example 3 is repeated except that the methylsulfinyl ethylammonium malate is replaced by the same amount of 2-methylsulfinyl ethylammonium nicotinate in one instance and by 2-methylsulfinyl ethylammonium salicylate in another.

EXAMPLE 4

Drinkable ampoules for use in the treatment of oily hair are prepared by admixing:

| | |
|---|---|
| 2-benzylsulfinyl ethyl-ammonium tartrate | 50 mg |
| Glucose | 300 mg |
| Water, q.s.p. | 5 ml |
| Orange juice, sufficient to flavor the composition | |

The administration orally of this product, at a rate of 2 ampoules per day for 15 days to a person exhibiting oily hair significantly improves the appearance of the scalp and hair.

EXAMPLE 5

A capillary lotion for use after shampooing on wet hair but before setting the hair is prepared by admixing:

| | |
|---|---|
| Copolymer of vinyl acetate/vinyl pyrrolidone | 1.5 g |
| 2-benzylsulfinyl ethyl-ammonium hydrochloride | 1 g |
| Perfume | 0.1 g |
| Ethyl alcohol, 25°, q.s.p. | 100 ml |

Example 5 is repeated except that the 2-benzylsulfinyl ethylammonium hydrochloride is replaced in one instance by 2-benzylsulfinyl ethylammonium nicotinate and by 2-benzylsulfinyl ethylammonium salicylate in another.

EXAMPLE 6

Orally administratable drops are prepared by mixing together:

| | |
|---|---|
| 2-β-hydroxyethylsulfinyl ethylurea | 0.75 g |
| Glycerine | 40 g |
| Ethyl alcohol | 30 g |
| Water, q.s.p. | 100 g |
| Lemon tincture (sufficient to flavor the composition) | |

The oral administration of this composition at a rate of 10 drops per day for 4 weeks to a person exhibiting oily hair and scalp significantly improves the appearance of the scalp and hair.

EXAMPLE 7

A cream for oily skin is prepared by admixing:

| | |
|---|---|
| 2-(2,2'-diethoxy ethylsulfinyl) ethylurea | 1.5 g |
| Quaternary ammonium | 0.3 g |
| Glycol stearate | 1 g |
| Cetyl alcohol | 4 g |
| Stearate polyoxyethylenated with 20 moles of ethylene oxide | 6 g |
| Isopropyl palmitate | 10 g |
| Calophyllum oil | 1 g |
| Preservative - parahydroxy benzoate | 0.3 g |
| Perfume, sufficient to aromatize the composition | |
| Sterile, demineralized water, q.s.p. | 100 g |

Daily application of this cream provides a clear improvement in the oily appearance of the skin.

Example 7 is repeated except that the active compound is advantageously replaced by the same amount of 2-(2,2'-dimethoxy ethylsulfinyl) ethylurea.

EXAMPLE 8

Lozenges for oral administration are prepared by admixing:

| | |
|---|---|
| 2-(2,3-dihydroxy propylsulfinyl) ethylurea | 50 mg |
| Lactose | 300 mg |
| Arabic gum, powder | 100 mg |
| Simple syrup, q.s.p. | 500 mg |

These lozenges taken at a rate of 2–3 per day, for 15 days, significantly improves the oily appearance of the hair.

EXAMPLE 9

A milk for oily skin is prepared by admixing:

| | |
|---|---|
| 2-methylsulfinyl ethylammonium 5-amino-3-thia hexanedioate | 0.5 g |
| Crosslinked polyacrylic acid, sold under the mark Carbopol 934 | 0.375 g |
| Isopropyl ester of the fatty acids of lanolin | 1 g |
| Oxyethylenated lanolin | 2.5 g |
| Oxyethylnated cetylstearyl alcohol | 3 g |
| Substituted alkylamide | 2 g |
| Triethanolamine, q.s.p. pH = 8 | |
| Methyl p-hydroxybenzoate | 0.1 g |
| Propyl p-hydroxybenzoate | 0.1 g |
| Water, q.s.p. | 100 ml |

EXAMPLE 10

Drinkable ampoules are prepared by admixing:

| | |
|---|---|
| 2-allylsulfinyl ethylurea | 250 mg |
| Glucose | 300 mg |
| Water, q.s.p. | 5 ml |
| Orange juice (sufficient to flavor the composition) | |

The oral administration of this product at a rate of 2 ampoules per day for 15 days to a person exhibiting an oily scalp due to hypersecretion of sebum significantly improves the appearance of the scalp and hair.

EXAMPLE 11

A shampoo powder is prepared by admixing the following components:

| | |
|---|---|
| Sodium lauryl sulfate | 40 g |
| Condensation product of fatty acids of copra and sodium isocyanate, sold under the name "HOSTAPON K.A." | 39 g |
| 2-benzylsulfinyl ethylurea | 2.5 g |
| Perfume | 1 g |

EXAMPLE 12

Lozenges which can be swallowed have the following compositions:

| | |
|---|---|
| 2-methylsulfinyl ethyl-ammonium malate | 50 mg |
| Lactose | 300 mg |
| Aromatic gum powder | 100 mg |
| Simple syrup, q.s.p. | 500 mg |

These lozenges, taken at a rate of two per day significantly reduce over a long period of time the oily appearance of the hair.

EXAMPLE 13

A fluid styling gel, capable of being used daily is prepared by admixing:

| | |
|---|---|
| 2-(2,2'-dimethoxy ethylsulfinyl) ethylammonium malate | 0.4 g |
| Copolymer of vinyl pyrrolidone and vinyl acetate | 2 g |
| Oxyethylenated lanolin | 1 g |
| Polyethylene glycol 300 | 5 g |
| Methyl p-hydroxybenzoate | 0.1 g |
| Propyl p-hydroxybenzoate | 0.1 g |
| Perfume | 0.1 g |
| Triethanolamine, q.s.p. pH = 8 | |
| Water, q.s.p. | 100 ml |

EXAMPLE 14

A dermatologic cake is prepared by admixing:

| 2-methylsulfinyl ethylurea | 2 g |
| --- | --- |
| Sodium alkane sulfonate sold under the mark Igepon A | 80 g |
| Liquid fraction of lanolin sold under the mark Lantrol | 12 g |
| Pur Cellin oil, branched esters of fatty acids | 2 g |
| Chlorinated antiseptic | 0.5 g |
| Titanium dioxide | 2 g |
| Perfume | 2.5 g |

EXAMPLE 15

A milk for oily skin is prepared by admixing:

| 2-benzylsulfinyl ethyl-ammonium tartrate | 2 g |
| --- | --- |
| Crosslinked polyacrylic acid, sold under the mark "Carbopol 934" | 0.375 g |
| Isopropyl ester of fatty acid of lanolin | 1 g |
| Oxyethylenated lanolin | 2.5 g |
| Oxyethylenated cetyl Stearyl alcohol | 3 g |
| Substituted alkylamide | 2 g |
| Triethanolamine, q.s.p. pH = 8 | |
| Methyl p-hydroxybenzoate | 0.1 g |
| Propyl p-hydroxybenzoate | 0.1 g |
| Water, q.s.p. | 100 g |

EXAMPLE 16

Consumable granules are prepared by admixing:

| 2-β-hydroxy ethylsulfinyl ethylurea | 2.5 g |
| --- | --- |
| Sucrose | 200 g |
| Lemon syrup | 50 g |

These granules, administered at a rate of a coffee spoonful twice a day significantly reduce the oily appearance of the scalp and hair.

EXAMPLE 17

In accordance with the present invention the following solution is prepared by admixing:

| Poly-(vinylpyrrolidone-vinyl acetate) resin sold under the mark "E 335" | 10 g |
| --- | --- |
| 2-benzylsulfinyl ethylurea | 0.5 g |
| Methylcellosolve | 2 g |
| Absolute ethyl alcohol, q.s.p. | 100 g |

30 g of the above solution are packaged in an aerosol container together with 49 g of trichlorofluoromethane and 21 g of dichlorodifluoromethane to provide a hair lacquer for oily hair.

This lacquer when applied regularly to oily hair progressively reduces its oily appearance. This formulation also possesses all the other qualities of a good hair lacquer.

EXAMPLE 18

A pearly, liquid shampoo is prepared by admixing the following components:

| Sodium lauryl sulfate oxy-ethylenated with 2.2 moles of ethylene oxide | 9 g |
| --- | --- |
| Sodium monolauryl sulfo-succinate | 1 g |
| Polyethyleneglycol distearate | 2 g |
| Lauryl diethanolamide | 2 g |
| 2-(2,3-dihydroxy propylsulfinyl) ethylammonium hydrochloride | 3 g |
| Perfume | 0.3 g |
| Water, q.s.p. | 100 g |

EXAMPLE 19

A cream shampoo is prepared by admixing the following components:

| Sodium lauryl sulfate | 12 g |
| --- | --- |
| Condensation product of fatty acids of copra and methyl taurine, a paste sold under the mark "HOSTAPON C.T" | 40 g |
| Lauryl monoethanolamide | 2 g |
| Glycerol monostearate | 4 g |
| 2-(2,2'-diethoxy ethylsulfinyl) ethylammonium malate | 1.5 g |
| Perfume | 0.2 g |
| Lactic acid, q.s.p. pH = 6.5 | |
| Water, q.s.p. | 100 g |

Example 19 is repeated except that the active compound is replaced by 2 g of 2-benzylsulfinyl ethylammonium 5-pyrrolidone-2-carboxylate.

EXAMPLE 20

A skin treating lotion is prepared by admixing:

| 2-methylsulfinyl ethylammonium hydrochloride | 2 g |
| --- | --- |
| Benzalkonium chloride | 0.2 g |
| Ethyl alcohol | 13 ml |
| Polyethylene glycol | 10 g |
| Perfume, sufficient to aromatize the composition | |
| Soluble dye, sufficient to color the composition | |
| Sterile, demineralized Water, q.s.p. | 100 g |

EXAMPLE 21

A cream for oily skin is prepared by admixing the following components:

| Polyoxyethylenated stearate | 3 g |
| --- | --- |
| Glycerol monostearate | 4 g |
| Cetyl alcohol | 7 g |
| Petrolatum oil | 8 g |
| Isopropyl myristate | 5 g |
| 2-benzylsulfinyl ethylurea | 8 g |
| Methyl p-hydroxybenzoate | 0.3 g |
| 1% solution of crosslinked polyacrylic acid, sold under the mark "Carbopol 941" | 40 g |
| Triethanolamine, q.s.p. pH = 6.5 | |
| Water, q.s.p. | 100 g |

This cream is applied to the scalp after shampooing. The scalp is then lightly massaged and the composition is permitted to remain in contact therewith for about 15 minutes after which the scalp and hair are rinsed.

Example 21 is repeated except that the active compound is advantageously replaced by the same amount of 2-allyl sulfinyl ethylurea.

EXAMPLE 22

A clear liquid shampoo is prepared by admixing the following components:

| | |
|---|---|
| Lauryl alcohol polyoxyethenated with 12 moles of ethylene oxide | 13 g |
| Copra diethanolamide | 4 g |
| Quaternized vinyl pyrrolidone copolymer sold under the name Gafquat 755 | 0.4 g |
| 2-methylsulfinyl ethylammonium malate | 1.5 g |
| Lactic acid, q.s.p. pH = 5 | |
| Perfume, sufficient to aromatize the composition | |
| Water, q.s.p. | 100 ml |

EXAMPLE 23

A liquid shampoo, which is left in contact with the hair for a period of 5 minutes before a final rinse, is prepared by admixing:

| | |
|---|---|
| Lauryl alcohol polyglycerolated with 4 moles of glycerol | 15 g |
| Quaternized vinyl pyrrolidone sold under the mark Gafquat 755 | 0.4 g |
| 2-methylsulfinyl ethylurea | 3 g |
| Polyethoxylated alkylamine sold under the mark Ethomeen 18/15 | 0.8 g |
| Lactic acid, q.s.p. pH = 6 | |
| Perfume, sufficient to aromatize the composition | |
| Water, q.s.p. | 100 ml |

EXAMPLE 24

A lotion is prepared by admixing the following components:

| | |
|---|---|
| 2-benzylsulfinyl ethylammonium 5-amino-3-thia hexanedioate | 2 g |
| Di-isobutylcresoxyethoxyethyl dimethylbenzylammonium chloride sold under the name Hyamine 10X. | 0.3 g |
| Salicylic acid | 0.2 g |
| Polyethylene glycol tertio-dodecylthioether | 0.1 g |
| Hydroxyethyl carboxymethyl 2-alkyl imidazolinium - sold under the mark Miranol C2M | 10 g |
| Perfume, sufficient to aromatize the composition | |
| Sterile, demineralized water, q.s.p. | 100 g |

EXAMPLE 25

A mask for oily skin is prepared by admixing:

| | |
|---|---|
| 2-methylsulfinyl ethylammonium 5-amino-3-thia hexanedioate | 1 g |
| Gelatin | 1 g |
| Fragacanth gum | 1 g |
| Bentonite | 4 g |
| Kaolin | 26 g |
| Titanium dioxide | 2 g |
| Camphor | 0.04 g |
| Dye, sufficient to color the composition | |
| Perfume, sufficient to aromatize the composition | |
| Sterile, demineralized water, q.s.p. | 100 g |

EXAMPLE 26

A treating mask for oily skin is prepared by admixing the following components:

| | |
|---|---|
| 2-methylsulfinyl ethylammonium malate | 0.5 g |
| Oxyethylenated lanolin | 5 g |
| Cetyl alcohol | 2 g |
| Self-emulsifiable ethylene glycol stearate | 7 g |
| Petrolatum - Codex | 5 g |
| Kaolin | 10 g |
| Titanium dioxide | 8 g |
| Preservative | 0.3 g |
| Water, q.s.p. | 100 g |

EXAMPLE 27

A lotion for combatting an oily appearance of the face is prepared by admixing the following components:

| | |
|---|---|
| 2-$\beta$-hydroxyethylsulfinyl ethylurea | 1 g |
| Ethyl alcohol | 16 g |
| Methyl p-hydroxy benzoate | 0.1 g |
| Propyl p-hydroxybenzoate | 0.1 g |
| Perfume, sufficient to aromatize the composition | |
| Dye, sufficient to color the composition | |
| Water, q.s.p. | 100 g |

EXAMPLE 28

A lotion for oily skin is prepared by admixing the following components:

| | |
|---|---|
| 2-benzylsulfinyl ethylammonium malate | 0.5 g |
| Pyrrolidone carboxylic acid, 50% | 3 g |
| Water soluble neo purcellin: branched esters of fatty acids polyethoxylated with 4 moles of ethylene oxide | 0.5 g |
| Perfume, sufficient to aromatize the composition | |
| Preservative | 0.2 g |
| Water, q.s.p. | 100 g |

Example 28 is repeated except that the 2-benzylsulfinyl ethylammonium malate is advantageously replaced by the same amount of 2-methylsulfinyl ethylammonium-5-pyrrolidone-2-carboxylate.

EXAMPLES OF PREPARATION

EXAMPLE 29

Preparation Of 2-benzylsulfinyl ethylammonium hydrochloride

A solution of 16.7 g of 2-benzylthio ethylamine in 100 ml of isopropanol, containing 5 ml of formic acid, is cooled with agitation, to 0° C. There are then slowly added 10 ml of $H_2O_2$ (110 volumes). The resulting mixture is permitted to stand for 12 hours at ambient temperature after which it is concentrated and treated with a mixture of ethanol and sulfuric ether saturated with gaseous HCl. The white precipitate (19 g), which forms, is filtered and then crystallized in ethanol, thus producing white crystals melting at 192° C.

Elemental Analysis – $C_9H_{14}ClNOS$

| | C | H | N | S |
|---|---|---|---|---|
| Calculated, % | 49.19 | 6.42 | 6.37 | 14.59 |
| Found, % | 49.12 | 6.14 | 6.50 | 14.79 |

EXAMPLE 30

Preparation Of 2-methylsulfinyl ethylammonium malate 5.5 ml of $H_2O_2$ (30%) are added to a suspension of 11.25 g of 2-methylthio ethylammonium malate in 50 ml of methanol. The temperature is reduced to 30° C during this addition. The solution obtained is agitated for 4 hours. The sulfoxide formed is precipitated by the addition of ethanol while cooling, yielding 11.2 g of a white product melting at 106° C.

Elemental Analysis — $C_{17}H_{15}NO_6S$

|  | C | H | N | S |
|---|---|---|---|---|
| Calculated, % | 34.84 | 6.26 | 5.80 | 13.29 |
| Found, % | 34.95 | 6.05 | 5.85 | 13.10 |

EXAMPLE 31

Preparation Of 2-methylsulfinyl ethylammonium hydrochloride

A solution of 1.82 g of 2-methylthio ethylamine in 20 ml of chloroform is agitated with 2 ml of $H_2O_2$ (110 volumes). When the exothermicity of the reaction ceases the absence of peroxide is verified and the reaction mixture is concentrated to dryness. The oily residue is treated with a solution saturated with gaseous HCl in ethanol. The product precipitates by the addition of sulfuric ether, yielding white crystals melting at 124° C.

Elemental Analysis — $C_3H_{10}ClNOS$

|  | C | H | N | S |
|---|---|---|---|---|
| Calculated, % | 25.10 | 6.97 | 9.75 | 22.29 |
| Found, % | 24.84 | 7.19 | 9.58 | 22.17 |

EXAMPLE 32

Preparation Of 2-benzylsulfinyl ethylammonium 5-amino-3-thio hexanedioate

A solution of 200 g of 2-benzylsulfinyl ethylamine, described in Example 29 above, in methanol is treated with a solution of 66 g of potash (85%) in methanol. The mixture is diluted with chloroform and the resulting potassium chloride precipitate is filtered. The remaining filtrate is then concentrated to dryness, yielding an oil residue (180 g) which is then dissolved in a liter of methanol. The resulting solution is brought to the boil and to it there are added 179 g of 5-amino-3-thia-hexanedioic acid with good agitation. The boiling solution is then filtered and the product crystallizes on cooling, providing white crystals melting at 148° C.

Elemental Analysis — $C_{14}H_{22}N_2O_5S_2$

|  | C | H | N | S |
|---|---|---|---|---|
| Calculated, % | 46.39 | 6.11 | 7.72 | 17.69 |
| Found, % | 46.10 | 6.08 | 7.71 | 17.62 |

EXAMPLE 33

Preparation of 2-benzylsulfinyl ethylurea

To a solution of 2-benzylthio ethylurea (0.03 mole) in 12 ml of formic acid, there are added 3 ml of $H_2O_2$ (110 volumes). The resulting solution is agitated for 2 hours while maintaining the temperature at 30° C. The solution is then concentrated under reduced pressure and the resulting oil residue, taken up in sulfuric ether, solidifies. The product obtained (4.8 g) is crystallized in acetonitrile and has a melting point of 110° C.

Elemental Analysis — $C_{10}H_{14}N_2O_2S$

|  | C | H | N | S |
|---|---|---|---|---|
| Calculated, % | 53.07 | 6.23 | 12.37 | 14.16 |
| Found, % | 53.17 | 6.07 | 12.44 | 14.07 |

EXAMPLE 34

Preparation Of 2-methylsulfinyl ethylurea

There are slowly added 3 ml of $H_2O_2$ (110 volumes) to a well agitated solution of 20 moles of 2-methylthio ethylurea in a mixture of ethanol and formic acid. The solution obtained is agitated for 2 hours after which it is concentrated under reduced pressure. The resulting residue is then crystallized in ethylacetate thus providing white crystals melting at 88° C. in a yield of 85%.

|  | C | H | N | S |
|---|---|---|---|---|
| Calculated, % | 31.98 | 6.71 | 18.65 | 21.34 |
| Found, % | 31.85 | 6.87 | 18.57 | 21.29 |

EXAMPLE 35

Preparation Of 2-allylsulfinyl ethylurea

To a solution of 1.6 g of 2-allythioethylurea in ethanol containing a little formic acid, there are added 1.2 cc of $H_2O_2$ (110 volumes) while cooling. After 12 hours of standing, the solution is then concentrated under vacuum and the residue is taken up in a mixture of isopropanol and ether. There is thus obtained a white powder melting at 66° C. in a yield of 59%.

Elemental Analysis — $C_6H_{12}N_2O_2S$

|  | C | H | N | S |
|---|---|---|---|---|
| Calculated, % | 40.88 | 6.86 | 15.89 | 18.19 |
| Found, % | 40.60 | 6.67 | 15.96 | 18.22 |

EXAMPLE 36

Preparation of 2-methylsulfinyl ethylammonium 5-amino-3-thia hexanedioate

This compound is prepared in accordance with the same procedures outlined in Example 32. A very hygroscopic white product is thus produced.

Elemental Analysis — $C_8H_{18}N_2O_5S_2$

|  | C | H | N | S |
|---|---|---|---|---|
| Calculated, % | 33.55 | 6.33 | 9.78 | 22.39 |
| Found, % | 33.55 | 6.57 | 9.59 | 22.38 |

EXAMPLE 37 Preparation of 2-(2,2'-diethoxy ethylsulfinyl) ethylammonium malate This compound is prepared in accordance with the same procedures outlined in Example 30.

The desired product in the form of a colorless oil with a 91% yield is thus obtained.

Elemental Analysis — $C_{12}H_{25}NO_8S$

|              | C     | H    | N    | S    |
|--------------|-------|------|------|------|
| Calculated, %| 41.97 | 7.33 | 4.07 | 9.33 |
| Found, %     | 41.80 | 7.49 | 3.90 | 9.15 |

EXAMPLE 38

Preparation of 2-(2,3-dihydroxy propylsulfinyl) ethylammonium hydrochloride

This compound is prepared in accordance with the same procedures set forth in Example 29.

White needle melting at 157° C. (methanol) are obtained.

Elemental Analysis — $C_5H_{15}ClNO_3S$

|              | C     | H    | N    | S     |
|--------------|-------|------|------|-------|
| Calculated, %| 29.48 | 6.92 | 6.87 | 15.74 |
| Found, %     | 29.29 | 6.96 | 7.04 | 15.95 |

EXAMPLE 39

Preparation of 2-methylsulfinyl ethylammonium nicotinate

To a solution, agitated at ambient temperature, of $5 \times 10^{-3}$ mole of 2-methylsulfinyl ethylamine in 5 cc of ethanol, there is added an equimolar amount of nicotinic acid in solution in the same volume of ethanol.

The agitation is maintained for 1 hour, after which the reaction mixture is concentrated under reduced pressure. The oil thus obtained is taken up in ether to which have been added some drops of ethanol.

After crystallization of the product, it is filtered and dried on phosphoric anhydride and under reduced pressure, thus yielding a white product melting at 94° C.

Elemental Analysis — $C_9H_{14}N_2O_3S$

|               | C     | H    | N     | S     |
|---------------|-------|------|-------|-------|
| Calculated, %.| 46.93 | 6.12 | 12.16 | 13.92 |
| Found, %      | 46.67 | 6.25 | 11.87 | 14.14 |

EXAMPLE 40

Preparation of 2-methylsulfinyl ethylammonium salicylate

This compound is obtained using the same conditions as those described in Example 39.

The oil obtained is crystallized in ethyl acetate, yielding a white product melting at 108° C.

Elemental Analysis — $C_{10}H_{15}NO_4S$

|              | C     | H    | N    | S     |
|--------------|-------|------|------|-------|
| Calculated, %| 48.96 | 6.16 | 5.71 | 13.07 |
| Found, %     | 48.77 | 6.13 | 5.82 | 12.99 |

EXAMPLE 41

Preparation of 2-benzylsulfinyl ethylammonium nicotinate

This compound is prepared in accordance with the same procedures as those described in Example 39.

White crystals having a melting point of 108° C. (ethanol-ether) are obtained.

Elemental Analysis — $C_{15}H_{18}N_2O_3S$

|              | C     | H    | N    | S     |
|--------------|-------|------|------|-------|
| Calculated, %| 58.80 | 5.92 | 9.14 | 10.46 |
| Found, %     | 58.65 | 5.87 | 9.15 | 10.40 |

EXAMPLE 42

Preparation of 2-benzylsulfinyl ethylammonium salicylate

This compound is prepared in accordance with the same procedures as described in Example 39.

White crystals having a melting point of 112° C. (acetonitrile) are obtained.

Elemental Analysis — $C_{16}H_{19}NO_4S$

|              | C     | H    | N    | S    |
|--------------|-------|------|------|------|
| Calculated, %| 59.79 | 5.95 | 4.35 | 9.97 |
| Found, %     | 59.89 | 5.93 | 4.41 | 10.09|

EXAMPLE 43

Preparation of 2-(2,3-dihydroxy propylsulfinyl) ethylurea

There is slowly added to an aqueous solution of potassium cyanate ($5 \times 10^{-3}$ mole) a solution of $5 \times 10^{-3}$ mole of 2-(2,3-dihydroxy propylsulfinyl) ethylamine hydrochloride in water. This mixture is agitated for 1 hour at a temperature lower than $-5°$ C. The mixture is then concentrated under reduced pressure and the resulting residue is taken up in methanol and filtered. The filtrate is evaporated and the residue is crystallized in a mixture of isopropanol and acetonitrile, yielding white crystals having a melting point of 102° C.

Elemental Analysis — $C_6H_{14}N_2O_4S$

|              | C     | H    | N     | S     |
|--------------|-------|------|-------|-------|
| Calculated, %| 34.37 | 6.71 | 13.32 | 15.25 |
| Found, %     | 34.29 | 6.78 | 13.28 | 14.99 |

TOXICITY STUDY OF THE COMPOUNDS OF FORMULA II

Tests which have been carried out have shown that the DLO of the compounds of formula II (lethal dose 0%: maximum dose administered in a single time, causing no mortality) was generally greater or equal to 3 g/kg for rats and mice.

As a comparison, the DLO of S-benzyl cysteamine hydrochloride is 400 mg/kg for mice and 500 mg/kg for rats and the DLO of S-methyl cysteamine hydrochloride is 1.5 g/kg for rats and mice.

Thus, the active compounds according to the invention provide greater security in use since they are more harmless than corresponding thioethers.

ACTIVITY TESTS ILLUSTRATING THE REDUCTION OF AN OILY APPEARANCE OF SKIN

The amount of skin lipids was determined after a treatment using the active compound tested below on animals (rats) exhibiting a seborrheic state resulting from a deficiency feeding in accordance with the method described by G. Aubin Et Coll., Parf. Coms. Sov. France, Vol. 1, No. 8, 1971.

| Active Compounds Tested | |
|---|---|
| $C_6H_5-CH_2-S-CH_2-CH_2-NH_2 \cdot HCl$ | (A) |
| $C_6H_5-CH_2-\underset{\underset{O}{\|\|}}{S}-CH_2-CH_2-NH_2 \cdot HCl$ | (B) |
| $C_6H_5-CH_2-\underset{O\phantom{XX}O}{S}-CH_2-CH_2-NH_2 \cdot HCl$ | (C) |

Skin lipids in mg/cm² (average values).

| Normal Animals | Seborrheic Animals | Seborrheic Animals Treated With: | | |
|---|---|---|---|---|
| | | A | B | C |
| 1580 | 2007 | 1531 | 1507 | 2009 |

It can be seen that the treatment of the seborrheic animals with B lowers the amount of skin lipids by 25%, i.e., to a value quite close to that of (A), whereas the same treatment using, instead, active compound C increases the lipid amount about 3%.

In view of the non-toxicity of B and its excellent activity it can readily be appreciated that this compound is ideally employed in topical and oral compositions for the stated purposes.

The present invention also relates to the compounds of formula II.

These compounds are produced reacting $H_2O_2$ with corresponding thioethers in a solvent or mixture of solvents selected from water, a lower alkanol, formic acid, acetic acid, or a chlorinated hydrocarbon such as chloroform. The temperature of the reaction is generally between −5 and 50° C.

What is claimed is:

1. A composition for treating oily hair or skin to reduce the oily appearance thereof comprising in an appropriate vehicle 0.1 to 10% by weight of an active compound having the formula:

$$R_1-\underset{\underset{O}{\|\|}}{S}-CH_2-CH_2-NH-R_2 \cdot HX$$

wherein $R_1$ represents a member selected from the group consisting of:

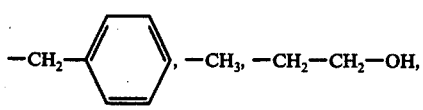

$-CH_2-\underset{OH}{CH}-CH_2-OH, \quad -CH_2-CH=CH_2$ and 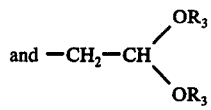

wherein
$R_3$ is lower alkyl containing 1-3 carbon atoms;
$R_2$ is hydrogen and
HX represents an organic acid selected from the group consisting of tartaric acid, malic acid, glutamic acid, salicylic acid, fumaric acid and 5-amino-3-thia hexanedioic acid.

2. The composition of claim 1 wherein said active compound is selected from the group consisting of
2-methylsulfinyl ethylammonium malate,
2-benzylsulfinyl ethylammonium tartrate,
2-(2,2'-dimethoxy ethylsulfinyl) ethylammonium malate,
2-(2,2'-diethoxy ethylsulfinyl) ethylammonium malate,
2-methylsulfinyl ethylammonium salicylate,
2-benzylsulfinyl ethylammonium salicylate,
2-benzylsulfinyl ethylammonium 5-amino-3-thia hexanedioate and
2-methylsulfinyl ethylammonium 5-amino-3-thia hexanedioate.

3. The composition of claim 1 wherein said active compound is present in an amount of 1 to 3 percent by weight based on the total weight of the composition.

4. The composition of claim 1 wherein said vehicle is water, an alcohol or a hydroalcoholic solution.

5. The composition of claim 4 wherein said alcohol is ethanol or isopropanol.

6. The composition of claim 1 which also includes an anionic, cationic, nonionic or amphoteric detergent.

7. The composition of claim 6 wherein said detergent is present in an amount of 4 to 20 percent by weight based on the total weight of the composition.

8. The composition of claim 6 wherein said detergent is present in an amount of 5 to 10 percent by weight based on the total weight of the composition.

9. The composition of claim 1 which also includes a cosmetic resin.

10. The composition of claim 9 wherein said cosmetic resin is present in an amount of 0.1 to 10 percent by weight based on the total weight of the composition.

11. The composition of claim 1 for topical application to the skin wherein said active compound is present in an amount of 0.1 to 5 percent by weight based on the total weight of the composition.

12. A process for treating oily hair and skin comprising topically applying thereto an effective amount of the composition of claim 1.

13. The compositon of claim 1 wherein said vehicle is a non-toxic ingestible carrier selected from the group consisting of water, a hydroalcoholic solution, a liquid food packaged in an ingestible capsule and a solid ingestible excipient.

14. A process for treating oily hair and skin comprising orally administering an effective amount of the composition of claim 13 to a person having oily hair or skin.

15. The process of claim 14 wherein said composition is administered for successive periods of 15 days with a 15 day interruption at a rate of 100 mg/24 hours.

16. A compound having the formula:

$$R_1-\underset{\underset{O}{\|\|}}{S}-CH_2-CH_2-NH-R_2 \cdot HX$$

wherein $R_1$ represents a member selected from the group consisting of:

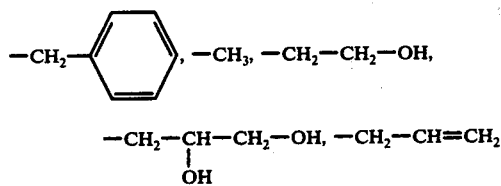

and 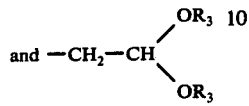

wherein
R$_3$ is lower alkyl containing 1-3 carbon atoms;
R$_2$ is hydrogen and
HX represents an organic acid selected from the group consisting of tartaric acid, malic acid, glutamic acid, salicylic acid, fumaric acid and 5-amino-3-thia hexanedioic acid.

17. The compound of claim 16 selected from the group consisting of:
2-methylsulfinyl ethylammonium malate,
2-benzylsulfinyl ethylammonium tartrate,
2-(2,2'-dimethoxy ethylsulfinyl) ethylammonium malate,
2-(2,2'-diethoxy ethylsulfinyl) ethylammonium malate,
2-methylsulfinyl ethylammonium salicylate,
2-benzylsulfinyl ethylammonium salicylate,
2-benzylsulfinyl ethylammonium 5-amino 3-thia hexanedioate and
2-methylsulfinyl ethylammonium 5-amino 3-thia hexanedioate.